United States Patent [19]

Gamon et al.

[11] Patent Number: 4,888,405

[45] Date of Patent: Dec. 19, 1989

[54] PREPARATION AND PROCESSING OF MIXTURE CONTAINING ORGANOCYCLOSILOXANES

[75] Inventors: Norbert Gamon, Seevetal; Christian Solbrig, Mehring-Öd; Karl Braunsperger, Burghausen, all of Fed. Rep. of Germany

[73] Assignee: Wacker-Chemie GmbH, Munich, Fed. Rep. of Germany

[21] Appl. No.: 230,398

[22] Filed: Aug. 10, 1988

[30] Foreign Application Priority Data

Aug. 14, 1987 [DE] Fed. Rep. of Germany ....... 3727182

[51] Int. Cl.$^4$ .............................................. C08G 77/06
[52] U.S. Cl. ..................................... 528/23; 525/477; 528/12; 528/16; 528/14; 528/15; 528/18; 528/19; 528/21; 528/33; 528/34; 528/37; 556/462; 556/467; 556/469

[58] Field of Search ...................... 528/34, 37, 23, 21, 528/18, 19, 15, 14, 33, 12, 16; 556/462, 467, 469; 525/477

[56] References Cited

U.S. PATENT DOCUMENTS

| | | | |
|---|---|---|---|
| 3,332,974 | 7/1967 | Bostick | 260/448.2 |
| 3,839,388 | 10/1974 | Nitzsche et al. | 528/23 |
| 3,903,047 | 9/1975 | Ashby | 528/37 |
| 3,998,865 | 12/1976 | Siciliano et al. | 260/448.2 |
| 4,482,670 | 11/1984 | Saam et al. | 528/23 |
| 4,704,443 | 11/1987 | Lamont | 528/18 |

Primary Examiner—Melvyn I. Marquis

[57] ABSTRACT

The invention relates to a process for treating organocyclosiloxane-containing mixtures with condensation catalysts. The resultant mixtures can be reacted with silanes or siloxanes to form organopolysiloxanes containing functional groups.

18 Claims, No Drawings

PREPARATION AND PROCESSING OF MIXTURES CONTAINING ORGANOCYCLOSILOXANES

The present invention relates to organocyclosiloxanes and more particularly to mixtures containing organocyclosiloxanes and to a process for converting the organocyclosiloxanes to organopolysiloxanes containing functional groups.

The invention relates to the preparation and further processing of mixtures having a high organocyclosiloxane content and a low content of hydroxyl groups bonded directly to silicon atoms.

In the preparation of linear polydiorganosiloxanes from, for example, diorganodihalosilanes, organocyclosiloxanes are produced as by-products and can be removed from the reaction mixture by distillation. The organocyclosiloxane-containing distillate can be equilibrated and/or condensed with other silanes or siloxanes and thus used, for example, as the starting material in the preparation of silicones containing reactive groups.

When such distillates are reacted with silanes containing reactive groups, the viscosities of the resultant products varied greatly depending on the quality of the distillates employed. This was attributable to the fact that the distillates also contain, in addition to the organocyclosiloxanes, varying amounts of short-chain, linear organosiloxanes having terminal hydroxyl groups bonded directly to silicon atoms.

Therefore, it is an object of the present invention to provide organocyclosiloxane-containing mixtures which are suitable as starting materials for silicones having reproducible viscosities. A further object of the present invention is to provide a process for preparing organopolysiloxanes containing functional groups.

SUMMARY OF THE INVENTION

The foregoing objects and others which will become apparent from the following description are accomplished in accordance with this invention, generally speaking, by providing a process for preparing organocyclosiloxane-containing mixtures which are suitable as starting materials for the preparation of silicones having controlled viscosities, which comprises treating a mixture containing organocyclosiloxanes and short-chain, linear organosiloxanes which is obtained as a distillate from the product mixture in the preparation of linear organopolysiloxanes with condensation catalyst(s). The resultant mixture thus obtainable is reacted with an organosilane or organosiloxane which contains at least one functional group and at least one group which is capable of condensation.

DESCRIPTION OF THE INVENTION

The mixture containing organocyclosiloxane and/or short-chain, linear organosiloxanes which are used as starting materials for the process of this invention are preferably those having the formula $$R_nSiO_{4-n/2} \quad \text{(I),}$$

in which R represents the same or different, hydrocarbon radicals or substituted hydrocarbon radicals having from 1 to 18 carbon atoms, or hydroxyl groups, and n represents an integer having a value of from 0 to 3 and an average value of from 1.9 to 2.

In particular, the mixture to be used as the starting material in the process of this invention comprises primarily organocyclosiloxanes of the formula $$(R_2SiO)_x \quad \text{(II),}$$

where x may have a value of from 3 to 20, and short-chain, linear organosiloxanes of the formula $$HO\text{—}(R_2SiO)_y\text{—}H \quad \text{(III),}$$

where R is the same as above and y may have values of from 1 to 20.

Examples of radicals represented by R are alkyl radicals, such as the methyl, ethyl, n-propyl, iso-propyl, n-butyl, isobutyl, tert-butyl, n-pentyl, iso-pentyl, neopentyl and tert-pentyl radicals, hexyl radicals, such as the n-hexyl radical, heptyl radicals, such as the n-heptyl radical, octyl radicals, such as the n-octyl radical, and iso-octyl radicals, such as the 2, 2, 4-trimethylpentyl radical, nonyl radicals, such as the n-nonyl radical, decyl radicals, such as the ndecyl radical, dodecyl radicals, such as the n-dodecyl radical, and octadecyl radicals, such as the n-octadecyl radical; alkenyl radicals, such as the vinyl and allyl radicals; cycloalkyl radicals, such as cyclopentyl, cyclohexyl, cycloheptyl and methylcyclohexyl radicals; aryl radicals, such as the phenyl, naphthyl, anthryl and phenanthryl radicals; alkaryl radicals, such as o-, m- and p-tolyl radicals, xylyl radicals and ethylphenyl radicals; and aralkyl radicals, such as the benzyl radical and the alpha- and β-phenylethyl radicals. Examples of substituted radicals represented by R are cyanoalkyl radicals, such as the β-cyanoethyl radical, and halogenated hydrocarbon radicals, for example, haloalkyl radicals, such as the 3, 3, 3-trifluoro-n-propyl radical, the 2, 2, 2, 2', 2', 2'-hexafluoroisopropyl radicals and the heptafluoroisopropyl radical, and haloaryl radicals, such as the o-, m- and p-chlorophenyl radicals.

The radicals represented by R are preferably the $C_1$- to $C_3$-alkyl, phenyl and/or vinyl radicals.

It is preferred that at least 80 percent, and more preferably at least 90 percent, of the radicals represented by R be methyl radicals.

The mixture to be used as the starting material for the process of this invention, which contains organocyclosiloxanes of formula (II) and short-chain, linear siloxanes of formula (III), is treated first with condensation catalyst(s). Examples of such condensation catalysts are primarily substances which are regarded as acids or bases in accordance with the definitions of Brönstedt or Lewis. These are heterogeneous catalysts, such as acid-activated bleaching earths and zeolites, and homogeneous catalysts. Examples of homogeneous, acidic catalysts are protonic acids, such as sulfuric acids, chlorosulfonic acid, selenic acid, nitric acid, phosphoric acids, boric acid, Lewis acids, such as iron(III) chloride, iron-(III) chloride hexahydrate, aluminum chloride, boron trifluoride, zinc chloride, tin(IV) chloride, phosphonitrile chlorides or reaction products thereof with organosilanes and/or organosiloxanes, and aluminum sulfate, or mixtures of at least two of these substances. Examples of basic catalysts are alkali metal hydroxides, in particular potassium hydroxide and cesium hydroxide, alkali metal silanolates, alkali metal alkoxides, quaternary ammonium hydroxides, such as tetramethylammonium hydroxide, benzyltrimethylammonium hydroxide, beta-hydroxyethyltrimethylammonium 2- ethylhexanoate, quaternary phosphonium hydroxides, such as tetra-n-butylphosphonium hydroxide and tri-n-butyl-3-[tris-(trimethylsiloxy)-silyl]-n-propyl-phosphonium hydroxide, potassium amide, amines and amine mixtures, and also mixtures of at least two of the substances or classes of substances mentioned as basic catalysts.

The amounts of the substances serving as catalysts depend on the choice of the substances employed as catalysts.

In the process of this invention, acidic catalysts, in particular phosphonitrile chlorides and reaction products thereof with organosilanes and/or organosiloxanes, are preferred.

The rate of addition of the condensation catalyst, the reaction temperature and the reaction time should be selected so that condensation predominantly occurs, i.e., in particular the terminal silanol groups of the compounds of formula (III), while equilibration, i.e., for example, cleavage of the siloxane bonds, inter alia, in the organocyclosiloxanes, only occurs to a very small extent.

If phosphonitrile chlorides are employed, preferably 1 ppm by weight to 1000 ppm by weight, more preferably from 5 ppm by weight to 100 ppm by weight, of phosphonitrile chlorides, based on the total weight of the organocyclosiloxane-containing mixture to be treated, are employed in the process of this invention. If products obtained from the reaction of phosphonitrile chlorides with organosilanes or organosiloxanes are employed as catalysts, then more catalyst should be employed.

Temperatures of from 0° C. to 150° C., preferably from 10° C. to 50° C., and reaction times of from 5 minutes to 48 hours, and more preferably from 15 minutes to 5 hours, are employed.

The treatment according to this invention with condensation catalyst(s) can be carried out at atmospheric pressure as well as at pressures above or below atmospheric pressure [0.1 MPa (abs.)]. Pressures of from 0.09 MPa (abs.) to 0.11 MPa (abs.) are preferred.

The condensation catalysts are preferably deactivated after treatment if the treated mixture is to be stored for a relatively long period. Deactivation as used herein, means in particular, removal from the mixture, for example, by filtration, if appropriate after prior adsorption or absorption on solids, and then rendered inert by chemical means, for example, by neutralization. Depending on the future use, the type of deactivation in the case of phosphonitrile chlorides can take place by neutralization using, or by adsorption or absorption on (with subsequent filtration) tertiary amines, n-butyllithium, lithium hydroxide, lithium carbonate, sodium carbonate, sodium hydrogen carbonate, potassium carbonate or potassium hydrogen carbonate, by means of solid oxides, hydroxides or carbonates of divalent or trivalent metals, such as Mg, Ca, Sr, Ba, Zn and Al, and also by means of basic ion exchangers. The mixtures treated in accordance with the process of this invention and preferably substantially free of active condensation catalyst generally contain no more than 0.1 percent of Si-bonded hydroxyl groups (determined by the method of Zerewitinoff).

The mixtures thus obtained can be used in preparing all polyorganosiloxanes which heretofore were possible to be prepared using organocyclosiloxanes. Examples of such poly-organosiloxanes are $\alpha$, $\omega$-bis-trimethylsiloxypolydimethylsiloxanes; $\alpha$, $\omega$-dihydroxypolydimethylsiloxanes; $\alpha$, $\omega$-dialkoxypolydimethylsiloxanes, and polyorganosiloxanes containing functional groups. Suitable functional groups are, in particular, SiC-bonded amino and/or mercapto radicals and/or groups carrying epoxide functions, vinyl and allyl radicals, SiC-bonded ethers and polyethers, acids, lactones, lactams and the like.

Preferred examples of such groups are the vinyl, beta-aminoethyl-gamma-aminopropyl, gamma-aminopropyl, gamma(cyclohexylamino)propyl, N-morpholinopropyl, glycidoxypropyl, mercaptopropyl and methacryloxy propyl groups.

The organopolysiloxanes carrying functional groups can be prepared by reacting mixtures which have been treated in the manner described above and containing organocyclosiloxanes with organosilanes or organosiloxanes having at least one functional group and at least one group which is capable of condensation. Examples of such groups which are capable of condensation are alkoxy groups, such as the methoxy and ethoxy groups, halogen radicals, in particular Si-bonded chlorine atoms, and acyloxy radicals, such as the acetoxy radical. Since they are more readily available, methoxy, ethoxy, methoxyethoxy, acetoxy and chlorine radicals are preferred.

The mixtures treated according to this invention are preferably reacted with silanes of the formula

$$R_q R'_r SiX_{(4-q-r)} \qquad (IV)$$

or with partial hydrolyzates thereof, where R is the same as above, R' represents the same or different SiC-bonded radicals containing hydrogen, up to 10 carbon atoms which may be substituted with nitrogen, oxygen and/or sulfur atoms; X represents the same or different groups which are capable of condensation, such as the methoxy, ethoxy, methoxyethoxy, acetoxy or chlorine groups; q is an integer having a value of 0, 1 or 2; and r is an integer having a value of 1, 2 or 3, and the sum of q and r is a maximum of 3. The sum of q and r is preferably a maximum of 2.

Preferred examples of silanes of formula (IV) are vinyltrichlorosilane, vinyltrimethoxysilane, vinyltriethoxysilane, vinyltris(methoxyethoxy)silane, vinyltriacetoxysilane, beta-aminoethyl-gamma-aminopropyltrimethoxysilane, beta- aminoethyl-gamma-aminopropyltriethoxysilane, beta-aminoethyl- gamma-aminopropylmethyldimethoxysilane, gamma-aminopropyltriethoxysilane, gamma-aminopropyltrimethoxysilane, gamma(cyclohexylamino)propyltriethoxysilane, gamma-(cyclohexylamino)-propyltrimethoxysilane, gamma-N-morpholinopropyltrimethoxysilane, methacryloxypropyl(trimethoxysilane), mercaptopropyltrimethoxysilane, 3-(triethoxysilylpropyl)succinic anhydride, methacryloxypropyltri(methoxyethoxy)silane, mercaptopropyltri(methoxyethoxy)silane, vinylmethyldimethoxysilane, mercaptopropylmethyldimethoxysilane, methacryloxypropylmethyldimethoxysilane, glycidoxypropyltriethoxysilane and the like.

The process of this invention for preparing polyorganosiloxanes having functional groups is preferably carried out at temperatures of from 0° C. to 250° C., and more preferably from 50° C. to 180° C.

Pressures of from 0.09 to 0.11 MPa (abs.) are preferred.

The process can be carried out in the presence of an inert solvent. The reaction mixture preferably contains less than 1 percent and more preferably less than 1 o/oo of solvent, based on its weight.

The reaction is preferably carried out in the presence of a catalyst which accelerates condensation and equilibration.

Examples of such catalysts have been described heretofore as examples of condensation catalysts.

If, in the process of this invention, an aminofunctional silane of the formula (IV) is employed, which is particularly preferred, basic catalysts, in particular tertiary ammonium hydroxides, are preferred as condensation and equilibration catalysts.

The mixtures containing organocyclosilanes which are treated in accordance with the procedure described above and in the examples, are just as good as the relatively expensive, pure organocyclosiloxanes, as starting materials in the preparation of organopolysiloxanes containing functional groups.

In the following examples, all amounts are by weight, unless otherwise specified. If no temperatures or pressures are indicated, the reactions were carried out at 25° C. and at 0.1 MPa (abs.). The Si-bonded hydroxyl groups were determined in each case by the method of Zerewitinoff.

EXAMPLE 1

About 0.08 ml of a 25 percent by weight solution of phosphonitrile chloride (30 ppm) in dichloromethane was added to 1000 g of an organocyclosiloxane-containing 0.26 percent by weight of Si-bonded hydroxyl groups, and the reaction mixture was allowed to stand at 25° C. for 1 hour. About 25 g of $NaHCO_3$ were added to the mixture, which had become turbid, and the mixture was dried using 25 g of anhydrous $Na_2SO_4$ and filtered. The content of hydroxyl groups in the filtrate was less than 0.1 percent by weight.

EXAMPLE 2:

About 0.056 ml of a 25 percent by weight solution of phosphonitrile chloride (30 ppm) in dichloromethane was added to 700 g of an organocyclosiloxane-containing 0.26 percent by weight of Si-bonded hydroxyl groups, the reaction mixture was stirred briefly and allowed to stand at 25° C. for 8 hours. About 14 g of $NaHCO_3$ were subsequently added, and the mixture was stirred for one hour and subsequently filtered. About 7.8 g of N-(2-aminoethyl)-3-aminopropylmethyldimethoxysilane and 0.3 ml of a 40 percent by weight methanolic solution of benzyltrimethylammonium hydroxide were added to 600 g of the filtrate, and the mixture was stirred for 1 hour at 80° C., and nitrogen was subsequently passed through the solution for 2 hours at 150° C. and at 2 kPa (abs.). About 525 g of a clear, colorless oil having a viscosity of 1,156 mPa.s at 25° C. and having an amine number of 0.14 were recovered as residue. (The amine number corresponds to the consumption of 1 N HCl in ml per g of sample weight on titration against tetrabromophthalein).

COMPARISON EXAMPLE 1

Example 2 was repeated, except that no phosphonitrile chloride was added. About 520 g of a clear, colorless oil having a viscosity of 62,400 mPa.s at 25° C. and having an amine number of 0.14 were obtained.

EXAMPLE 3

About 700 g of an organocyclosiloxane-containing mixture, which differed from that used in the previous examples including its content of Si-bonded hydroxyl groups, were treated in accordance with Example 2. About 520 g of a clear, colorless oil having a viscosity of 1,038 mPa.s at 25° C. were obtained.

COMPARISON EXAMPLE 2

Example 3 was repeated, except that no phosphonitrile chloride was added. About 515 g of a clear, colorless oil having a viscosity of 12,000 mPa.s at 25° C. were obtained.

COMPARISON EXAMPLE 3

Example 2 was repeated, except that 600 g of octamethylcyclotetrasiloxane were substituted for the 600 g of the filtrate of the solution treated with phosphonitrile chloride and sodium hydrogen carbonate. About 532 g of a clear, colorless oil having a viscosity of 946 mPa.s at 25° C. were obtained.

What is claimed is:

1. A process for preparing an organocyclosiloxane-containing mixture which is suitable as the starting material in the preparation of silicones having a reproducible viscosity, which comprises treating with a condensation catalyst a mixture containing organocyclosiloxanes and short-chain, linear organopolysiloxanes which is obtained as distillate from the product mixture formed in the preparation of linear organopolysiloxanes.

2. The process of claim 1, wherein the condensation catalyst is subsequently deactivated.

3. The process of claim 1, wherein the condensation catalyst is subsequently removed from the mixture.

4. The process of claim 1, wherein at least 80 percent of the number of the organic groups in the organocyclosiloxanes and short-chain, linear organosiloxanes which are bonded directly to a silicon atom are methyl groups.

5. The process of claim 1, wherein the condensation catalyst is phosphonitrile chlorides.

6. The process of claim 2, wherein the condensation catalyst is phosphonitrile chlorides.

7. The process of claim 3, wherein the condensation catalyst is phosphonitrile chlorides.

8. A process for preparing a polyorganosiloxane containing functional groups, which comprises reacting the mixture obtained from claim 1 with an organosilicon compound selected from the group consisting of an organosilane and an organosiloxane, each of which contains at least one functional group and at least one group which is capable of condensation.

9. A process for preparing a polyorganosiloxane containing functional groups, which comprises reacting the mixture obtained from claim 2 with an organosilicon compound selected from the group consisting of an organosilane and an organosiloxane, each of which carries at least one functional group and at least one group which is capable of condensation.

10. A process for preparing a polyorganosiloxane containing functional groups which comprises reacting the mixture obtained from claim 3 with an organosilicon compound selected from the group consisting of an organosilane and an organosiloxane, each of which carries at least one functional group and at least one group which is capable of condensation.

11. A process for preparing a polyorganosiloxane containing functional groups which comprises reacting the mixture obtained from claim 5 with an organosilicon compound selected from the group consisting of an organosilane and an organosiloxane, each of which carries at least one functional group and at least one group which is capable of condensation.

12. The process of claim 8, wherein the organosilicon compound is an organosilane of the formula $$R_qR'_rSiX_{(4-q-r)} \quad (IV)$$

or an organosiloxane which is a partial hydrolyzate of said organosilane in which R is selected from the group consisting of hydrocarbon radicals and substituted hydrocarbon radicals having from 1 to 18 carbon atoms, R' represents SiC-bonded radicals containing hydrogen, up to 10 carbon atoms which may be substituted with atoms selected from the group consisting of nitrogen, oxygen and sulfur atoms; X represents condensible groups; q is an integer having a value of 0, 1 or 2; and r is an integer having a value of 1, 2 or 3; and the sum of q and r is a maximum of 3.

13. The process of claim 9, wherein the organosilicon compound is an organosilane of the formula $$R_qR'_rSiX_{(4-q-r)} \quad (IV)$$

or an organosiloxane which is a partial hydrolyzate of said organosilane in which R is selected from the group consisting of hydrocarbon radicals and substituted hydrocarbon radicals having from 1 to 18 carbon atoms, R' represents SiC-bonded radicals containing hydrogen, up to 10 carbon atoms which may be substituted with atoms selected from the group consisting of nitrogen, oxygen and sulfur atoms; X represents condensible groups; q is an integer having a value of 0, 1 or 2; and r is an integer having a value of 1, 2 or 3; and the sum of q and r is a maximum of 3.

14. The process of claim 10, wherein the organosilicon compound is an organosilane of the formula $$R_qR'_rSiX_{(4-q-r)} \quad (IV)$$

or an organosiloxane which is a partial hydrolyzate of said organosilane in which R is selected from the group consisting of hydrocarbon radicals and substituted hydrocarbon radicals having from 1 to 18 carbon atoms, R' represents SiC-bonded radicals containing hydrogen, up to 10 carbon atoms which may be substituted with atoms selected from the group consisting of nitrogen, oxygen and sulfur atoms; X represents condensible groups; q is an integer having a value of 0, 1 or 2; and r is an integer having a value of 1, 2 or 3; and the sum of q and r is a maximum of 3.

15. The process of claim 8, wherein the organosilane is an aminofunctional organosilane.

16. The process of claim 8, wherein the organosiloxane is an aminofunctional organosiloxane.

17. The process of claim 9, wherein the organosilane is an aminofunctional organosilane.

18. The process of claim 9, wherein the organosiloxane is an aminofunctional organosiloxane.

* * * * *